United States Patent [19]

Pope

[11] Patent Number: 5,286,453
[45] Date of Patent: Feb. 15, 1994

[54] DEVICE FOR DISPENSING A BIOLOGICAL FLUID FROM A SEALED VACUUM TUBE

[76] Inventor: Carolyn M. Pope, 14 Lake Forest Dr., Taylorsville, N.C. 28681

[21] Appl. No.: 861,776

[22] Filed: Apr. 2, 1992

[51] Int. Cl.[5] .......................... B01L 3/02; A61B 19/00
[52] U.S. Cl. .................................... 422/100; 128/763; 422/99; 604/201; 604/205; 604/239; 604/283; 604/411; 604/412
[58] Field of Search ............... 604/201, 205, 239, 283, 604/411, 412, 905; 128/763, 764; 436/40; 422/99, 100

[56] References Cited

U.S. PATENT DOCUMENTS

| | | | |
|---|---|---|---|
| 3,171,446 | 3/1965 | Koch | 141/24 |
| 3,420,107 | 1/1969 | Rowett | 73/425.6 |
| 3,592,245 | 7/1971 | Devon et al. | 141/25 |
| 3,873,271 | 3/1975 | Young et al. | 436/40 |
| 4,300,404 | 11/1981 | Mehl et al. | 73/863.52 |
| 4,671,330 | 6/1987 | Miles | 141/24 |
| 4,786,471 | 11/1988 | Jones et al. | 422/61 |
| 4,927,605 | 5/1990 | Dorn et al. | 422/102 |
| 5,037,549 | 8/1991 | Ballies | 210/515 |

Primary Examiner—James C. Housel
Assistant Examiner—Milton I. Cano
Attorney, Agent, or Firm—Richard E. Jenkins

[57] ABSTRACT

A device for dispensing a portion of a biological liquid from a sealed vacuum tube onto a microscopic slide or other suitable application wherein the device is formed from an open-ended elongate housing having a cannula mounted therein so as to extend in a longitudinal direction thereof with a first needle end located in the upper portion to pierce the stopper of a vacuum tube and a second needle end positioned in the lower portion of the housing. A protuberance is provided at the base of the first needle end which serves to act as a pump in conjunction with the stopper of a vacuum tube momentarily pushed thereagainst so as to force a predetermined portion of a biological liquid in the tube through the cannula and out of the lower needle end thereof.

6 Claims, 4 Drawing Sheets

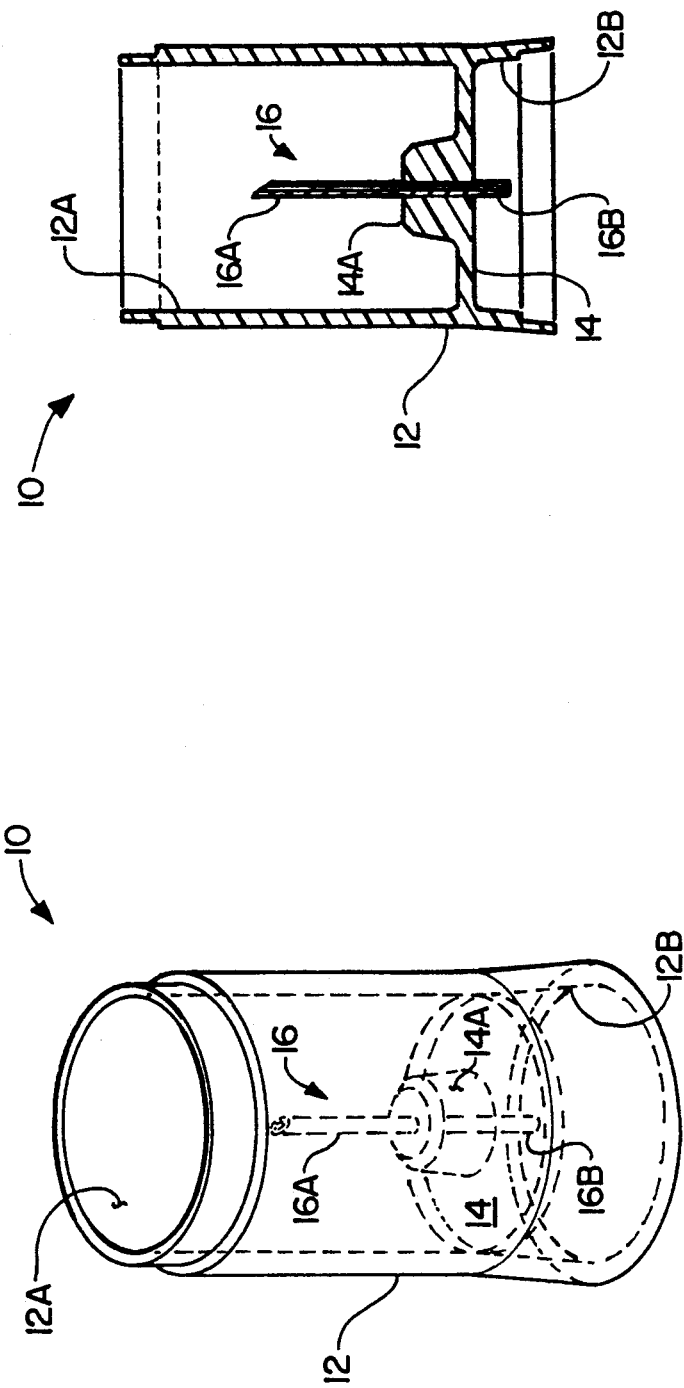

DEVICE FOR DISPENSING A BIOLOGICAL FLUID FROM A SEALED VACUUM TUBE

DESCRIPTION

1. Technical Field

The present invention relates to a device for dispensing a biological fluid from a sealed vacuum tube and more particularly to a device for dispensing a portion of a potentially hazardous biological liquid from a sealed vacuum tube onto a slide for microscopic examination or the like.

2. Related Art

Examination of a peripheral blood smear is one of the most basic hematologic procedures and many hematologic diagnoses depend upon a properly smeared and stained blood film on a microscopic glass slide. In many cases a definitive diagnosis can be established solely on a basis of microscopic examination of a smeared glass slide. Conventionally, a blood smear is prepared by placing a small drop of anticoagulated blood (blood mixed with EDTA) near one end of a clean glass slide and then using a second slide as a spreader in order to create a thin, air-dried blood film.

Unfortunately, in order to obtain a drop of blood for placement on a glass slide, it is presently necessary for a technologist in a hematology laboratory to remove the stopper from a vacuum tube containing the blood sample of interest in order to gain access to the blood within the tube. The procedure of removing and replacing the rubber stopper on the vacuum tube gives rise to the possibility of exposure of the technologist to the blood sample in a number of ways (e.g., blood aerosolization, blood spillage and/or glove contamination with the blood).

As is well known to those working in this type of laboratory environment, the blood sample many times is a potentially hazardous blood sample since it may have come from a patient suspected of having a variety of diseases or infections including the AIDS virus. Techniques which are presently utilized for the transfer of a drop of blood from the vacuum tube to the microscopic glass slide include using an applicator stick, capillary tube or the rubber stopper top of the tube for placement of a drop of blood from the tube onto the glass slide. All of the above techniques require a two-handed manipulation of the vacuum tube and the transfer device which poses a risk of exposing the technologist to the potentially hazardous blood sample. Moreover, these techniques pose the risk of additional contamination of the blood transfer devices which can present subsequent problems such as cross-contamination and disposal difficulties related to contaminated items.

Recently, automated closed blood sampling systems have been developed for the hematology laboratory such as the CELL-DYN 3000 and COULTER STKS. These new hematology analyzers are designed for in vitro diagnostic use in clinical laboratories where EDTA anticoagulated whole blood is analyzed by the equipment.

With the advent of the closed sampling systems represented by these machines, visual examination of a peripheral glass slide smear is now only performed on those specimens that generate results from the automated equipment that fall outside of a predetermined statistically "normal" range. Therefore, the aforementioned type of closed sampling automated equipment can process "normal" whole blood specimens in vacuum tubes without requiring removal of the rubber stopper. Only the specimens that are statistically "abnormal" must be opened, and thus the hematology laboratory technologist is faced with the problem of being required to open only those "high risk" tubes with abnormal initial testing results in order to prepare blood smears for microscopic visual examination thereof to confirm or reject the original testing results. These particular vacuum tubes logically can be assumed to be more likely to contain hazardous agents therein in view of their "abnormal" status as determined by the automated closed sampling equipment than the whole blood samples that fall within the statistically "normal" range and which do not require additional visual analysis subsequent to analyzation on the automated closed sampling equipment.

Thus, there is a long-felt need for a device which will allow for forming a blood smear on a glass slide without having to open a vacuum tube containing a potentially hazardous blood sample so as to reduce the risk to the technologist charged with preparing the slide.

DISCLOSURE OF THE INVENTION

In accordance with the present invention, applicant provides a device for dispensing a portion of a potentially hazardous biological liquid from a sealed vacuum tube onto a slide for microscopic examination or the like. The device comprises an elongate housing having an open-ended upper portion and an open-ended lower portion. A cannula is mounted in the housing and extends in the longitudinal direction thereof with a first needle end positioned in the upper portion of the housing to pierce the stopper of an air evacuated tube when the tube is inverted and forced thereagainst, and a second needle end is positioned in the lower portion of the housing and terminates short of the bottom thereof. A protuberance at the base of the first needle end serves to urge the stopper of the air evacuated tube momentarily inwardly when the tube is pushed thereagainst so as to force a predetermined portion of a potentially hazardous biological liquid contained within the tube through the cannula and out of the second needle end onto a glass slide for microscopic examination or the like.

It is therefore the object of this invention to provide a device adapted to obtain a drop of whole blood from a vacuum tube and place the blood sample onto a glass slide without requiring removal of the tube stopper.

It is another object of the present invention to provide a device which minimizes the risk of a technologist in handling a vacuum tube containing a potentially hazardous blood sample therein from which a peripheral blood smear must be obtained.

It is still another object of the present invention to provide an inexpensive device which expedites and simplifies the process of safely obtaining a drop of blood from a vacuum tube containing whole blood and forming a peripheral blood smear therewith.

Some of the objects of the invention having been stated, other objects will become evident as the description proceeds, when taken in connection with the accompanying drawings.

BRIEF DESCRIPTION OF THE DRAWINGS

FIG. 1 is a perspective view of the device of an embodiment of the present invention;

FIG. 2 is a vertical cross-sectional view of the device of FIG. 1;

BEST MODE FOR CARRYING OUT THE INVENTION

Figure 3:
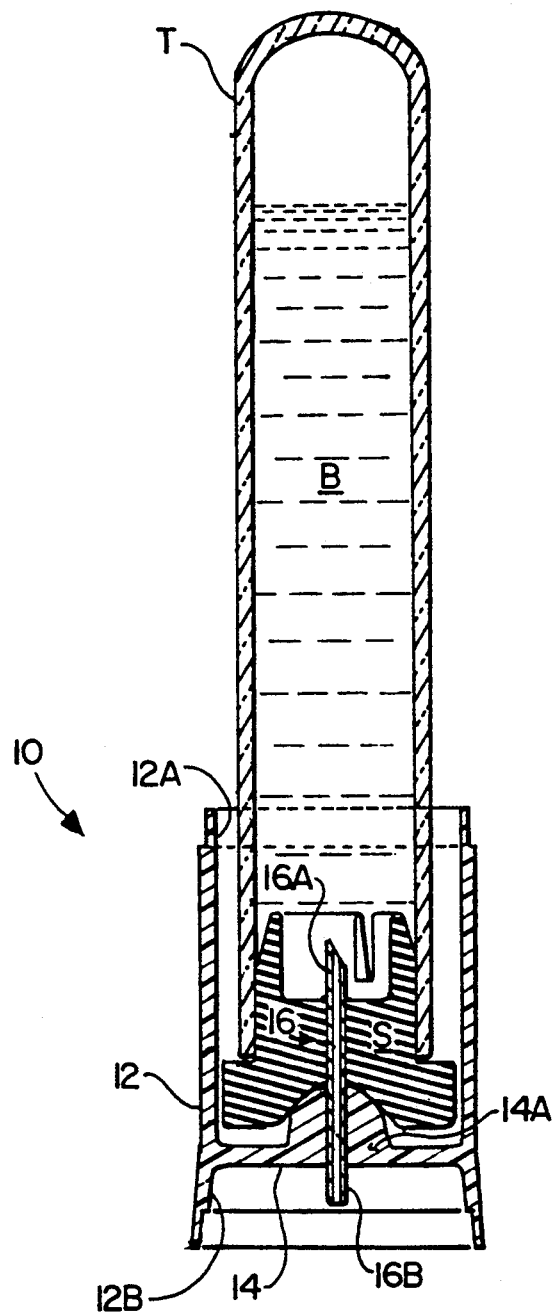
FIG. 3 is a view similar to FIG. 2 but with the stopper of an inverted air-evacuated tube forced over the upper end of the cannula positioned in the device.

Referring now more specifically to the drawings, FIGS. 1 and 2 show a preferred embodiment of the device of the invention, generally designated 10. Device 10 comprises a cylindrical housing (preferably formed from polyethylene) and generally designated 12. Housing 12 includes transverse support 14 extending thereacross which separates housing 12 into upper portion 12A and lower portion 12B and fixedly supports cannula 16 coaxially within housing 12. Transverse support 14 serves to mount cannula 16 so that upper needle end 16A extends into upper housing portion 12A so as to pierce the rubber stopper of an air evacuated tube when the tube is inverted and forced against the sharpened end thereof. Second needle end 16B extends through support 14 and is positioned in lower portion 12B of housing 12. As can be seen in FIGS. 1 and 2, upper needle end 16A terminates short of the top edge of upper housing portion 12A so as to minimize the likelihood of needle end 16A inflicting a puncture wound on a user of device 10, and lower needle end 16B terminates short of the lower edge of housing lower portion 12B so as to allow a drop of blood to form on the end thereof and be deposited onto a glass slide for microscopic examination. The specifics of the construction of device 10 as well as the preferred technique for use thereof will be explained in more detail hereinbelow.

Finally, still referring to FIGS. 1 and 2, it can be seen that an upwardly tapered or dome-shaped protuberance 14A is formed at the base of upper needle end 16A which in conjunction with the stopper of a vacuum tube inserted into upper portion 12A of device 10 acts as a pump when downward pressure is applied to the vacuum tube to force a drop of blood through lower needle end 16B of cannula 16 onto a glass slide positioned beneath device 10. Although protuberance 14A is shown in a specific configuration in FIGS. 1-5, it should be appreciated that virtually any shape of protuberance could be utilized which would serve as a pump in conjunction with the rubber stopper of a vacuum tube. Thus, the invention described herein is contemplated as encompassing any size and shape of protuberance 14A which would serve to effectuate this function.

Although many different configurations of device 10 can be constructed in accordance with the present invention, the dimensions of a representative device are set forth in Table 1 as follows:

TABLE 1

| Inside Diameter At Top | 18 millimeters |
| Inside Diameter at Base | 20 millimeters |
| Needle Gauge | 20 |

TABLE 1-continued

| Distance from tip of upper needle end to top of upper housing | 9 millimeters |
| Distance from tip of lower needle end to bottom of lower housing | 2 millimeters |
| Length of upper needle end above protuberance | 12 millimeters |
| Length of lower needle end | 2 millimeters |
| Height of protuberance | 8 millimeters |
| Diameter of protuberance at base | 6 millimeters |

Figure 4:
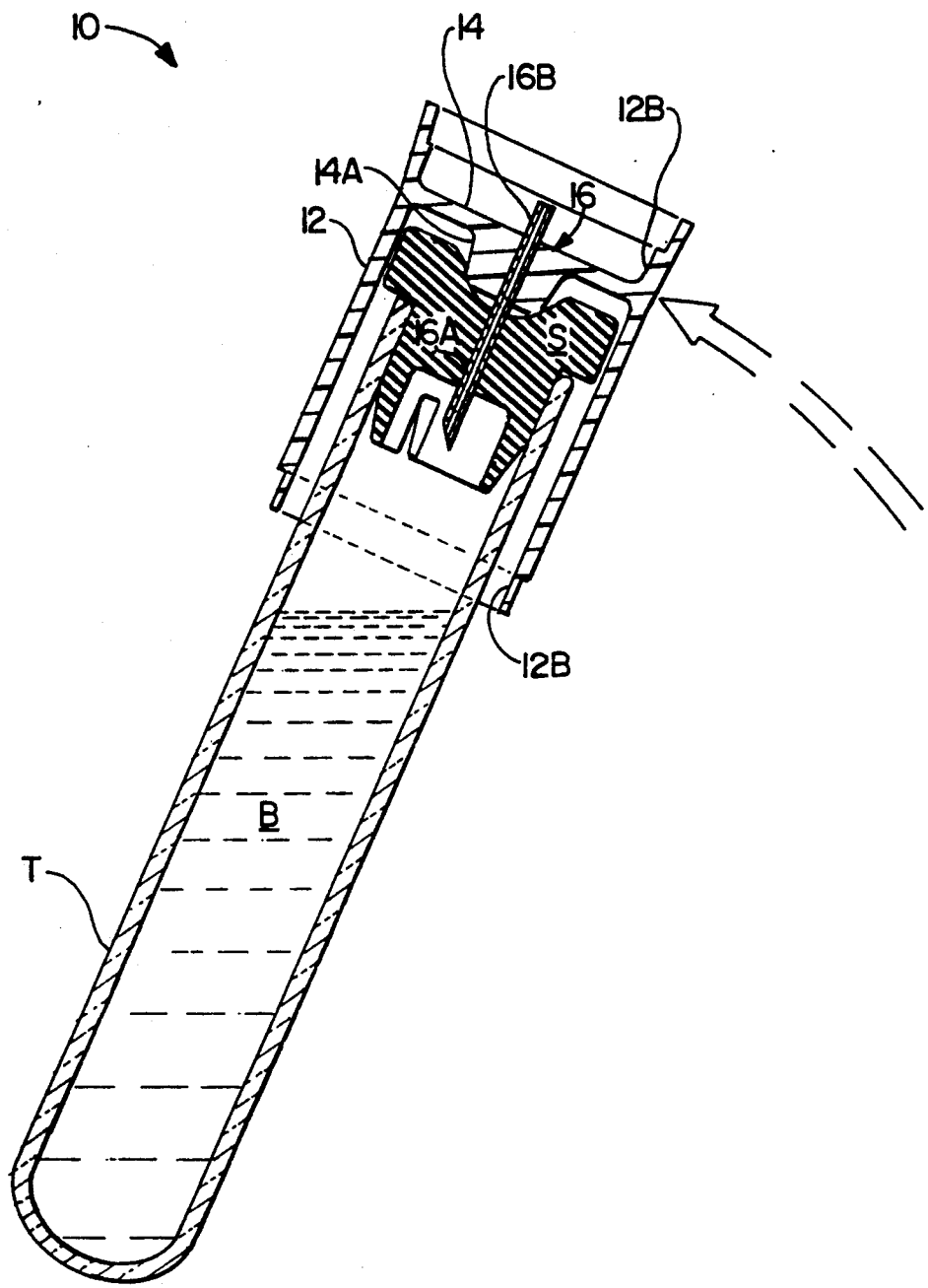
FIG. 4 is a view similar to FIG. 3 wherein the air evacuated tube containing a whole blood sample is inverted so as to provide for venting of residual vacuum in the tube and equalization of pressure between the inside of the tube and the environment surrounding the tube.
Figure 5:
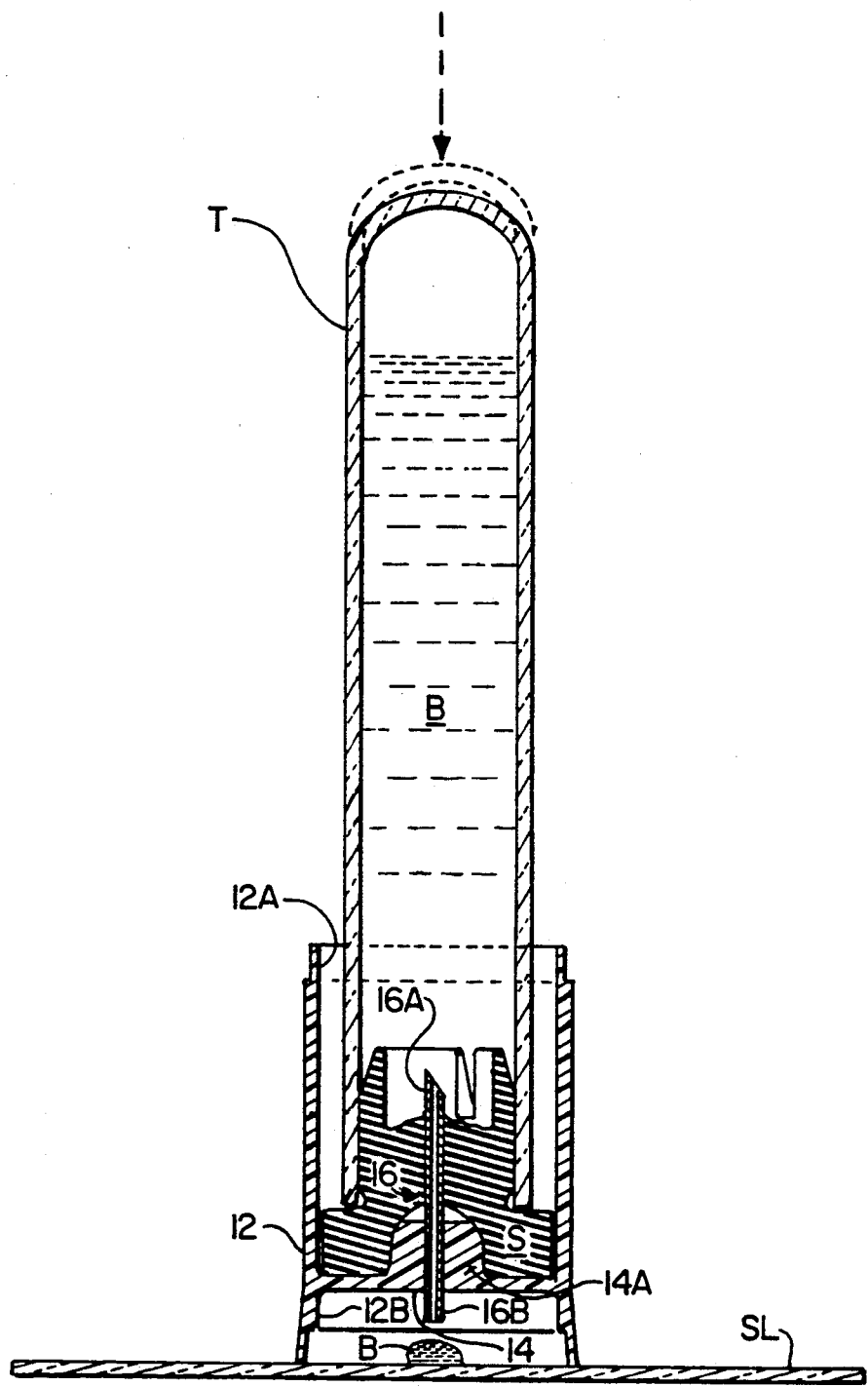
FIG. 5 is a view similar to FIG. 3 wherein the air evacuated tube has been momentarily pressed downwardly against the protuberance at the base of the upper end of the cannula and a drop of blood forced from the tube and onto the glass slide positioned therebeneath.

In use, which can best be appreciated with reference to FIGS. 3–5, applicant contemplates an EDTA vacuum tube T containing whole blood will be inserted into upper housing portion 12A of device 10 until upper needle end 16A pierces rubber stopper S (see FIG. 3). In order to equalize the pressure between vacuum tube T and the outside environment, tube T is inverted with device 10 attached thereto so as to expose upper needle end 16A (see FIG. 4) and thus allow the interior pressure of tube T to equalize with the environmental pressure through cannula 16. Finally, the bottom end of device 10 is suitably positioned on a glass slide SL (see FIG. 5) and a downward force applied to tube T which serves to force a drop of blood B from lower needle end 16B onto slide SL.

The slight downward movement of tube T relative to protuberance 14A of device 10 serves to create a pumping effect by causing the upward displacement of flexible rubber stopper S so as to increase the pressure within tube T and force a drop of blood B through cannula 16. Termination of the downward force on tube T terminates the flow of blood, and a suitable peripheral blood smear may be prepared from blood drop B on glass slide SL. Once device 10 has served its useful function, it is contemplated that it would then be discarded into an appropriate hazardous waste disposal container either with or without tube T secured thereto.

Although device 10 has been described herein for use to obtain a drop of blood from a vacuum tube to make a blood smear, applicant contemplates that the device of the invention has many other applications for use and thus the invention is in no way intended to be limited to the representative use described herein but is contemplated by applicant for use in any suitable application (e.g., obtaining urine samples from a vacuum tube, etc.)

It will be understood that various details of the invention may be changed without departing from the scope of the invention. Furthermore, the foregoing description is for the purpose of illustration only, and not for the purpose of limitation—the invention being defined by the claims.

What is claimed is:

1. A device for dispensing a portion of a biological liquid from a sealed vacuum tube, said device comprising:

a vacuum tube at least partially filled with a biological fluid, said tube being closed at one end and sealed at the other end by a flexible pierceable stopper;

an elongated housing having an open-ended upper portion and an open-ended lower portion;

a cannula mounted in said housing and extending in the longitudinal direction thereof with a first needle end being positioned in the upper portion of said housing to pierce said stopper of said tube when the tube is inverted and forced thereagainst, and a second needle end being positioned in the lower portion of said housing and terminating short of the bottom thereof; and means for forcing said biological fluid out of said tube and through said cannula, said forcing means being positioned at the base of said first needle end and adapted to urge said stopper of said tube momentarily inwardly when said tube is pushed thereagainst;

whereby subsequent to piercing of said stopper, said tube can be inverted and pushed against said forcing means so as to force a predetermined portion of the biological liquid therein through said cannula and out of said second needle end.

2. A device according to claim 1 wherein said elongate housing comprises a cylindrical element having a transversely extending support positioned therein for fixedly mounting said cannula with the first needle end extending thereabove and the second needle end extending therebelow.

3. A device according to claim 2 wherein said support is positioned between said upper portion and said lower portion of said cylindrical element and said cannula is mounted to said support so as to extend substantially coaxially within said cylindrical element.

4. A device according to claim 2 wherein said first needle end extends about 12 millimeters in length and terminates about 9 millimeters short of the top of the housing upper end and said second needle end extends about 2 millimeters in length and terminates about 2 millimeters short of the bottom of the housing lower portion.

5. A device according to claim 1 wherein said forcing means comprises an upwardly tapered element.

6. A device according to claim 5 wherein said forcing means comprises a dome-shaped element having a height of about 8 millimeters and a base diameter of about 6 millimeters.

* * * * *